(12) United States Patent
Msika et al.

(10) Patent No.: US 10,444,226 B2
(45) Date of Patent: Oct. 15, 2019

(54) CORNEODESOMOSOMES AND BARRIER FUNCTION MATURATION

(71) Applicant: LABORATOIRES EXPANSCIENCE, Courbevoie (FR)

(72) Inventors: Philippe Msika, Versailles (FR); Nadège Lachmann, Leymen (FR); Caroline Baudouin, Rambouillet (FR)

(73) Assignee: LABORATOIRE EXPANSCIENCE, Courbevoie (FR)

( * ) Notice: Subject to any disclaimer, the term of this patent is extended or adjusted under 35 U.S.C. 154(b) by 477 days.

(21) Appl. No.: 14/915,702

(22) PCT Filed: Sep. 3, 2014

(86) PCT No.: PCT/EP2014/068722
§ 371 (c)(1),
(2) Date: Mar. 1, 2016

(87) PCT Pub. No.: WO2015/032808
PCT Pub. Date: Mar. 12, 2015

(65) Prior Publication Data
US 2016/0195515 A1    Jul. 7, 2016

(30) Foreign Application Priority Data
Sep. 3, 2013 (EP) .................................. 13182839

(51) Int. Cl.
| G01N 31/00 | (2006.01) |
| G01N 33/53 | (2006.01) |
| G01N 33/50 | (2006.01) |
| G01N 33/68 | (2006.01) |

(52) U.S. Cl.
CPC ..... *G01N 33/5044* (2013.01); *G01N 33/5023* (2013.01); *G01N 33/6881* (2013.01); *G01N 2333/47* (2013.01)

(58) Field of Classification Search
None
See application file for complete search history.

(56) References Cited

PUBLICATIONS

Haftek et al. (British Journal of Dermatology, 1997, vol. 137, pp. 864-873).*
Simon et al. (The Journal of Biological Chemistry, vol. 276, No. 23, Jun. 8, 2001, pp. 20292-20299).*
Tascilar et al. (Annals of Oncology 10.Suppl. 4:S107-S110, 1999).*
Tockman etal. (Cancer Research 52:2711s-2718s, 1992).*
Igawa etal. (Journal of Dermatological Science, 72, 2013, pp. 54-60).*
Fluhr et al., "Functional Consequences of a Neutral pH in Neonatal Rat Stratum Corneum," Journal of Investigative Dermatology, vol. 123, No. 1, pp. 140-151, Jul. 2004.
Fluhr et al., "Topical Peroxisome Proliferator Activated Receptor Activators Accelerate Postnatal Stratum Corneum Acidification," Journal of Investigative Dermatology, vol. 129, No. 2, pp. 365-374, Aug. 2008.
Harding, "The cornified cell envelope: an important marker of stratum corneum maturation in healthy and dry skin," International Journal of Cosmetic Science, vol. 25, No. 4, pp. 157-167, Aug. 2003.
Igawa et al., "Aberrant distribution patterns of corneodesomosmal components of tape-stripped corneocytes in atopic dermatitis and related skin conditions (ichthyosis vulgaris, Netherton syndrome and peeling skin syndrome type B)," Journal of Dermatological Science, vol. 72, No. 1, pp. 54-60, Jun. 2013.
Naoe et al., "Bidimensional analysis of desmoglein 1 distribution on the outermost corneocytes provides the structural and functional information of the stratum corneum," Journal of Dermatological Science, vol. 57, No. 3, pp. 192-198, Mar. 2010.
Oyama et al., "New non-invasive method for evaluation of the stratum corneum structure in diseases with abnormal keratinization by immunofluorescence microscopy of desmoglein 1 distribution in tape-stripped samples," The Journal of Dermatology, vol. 37, No. 10, pp. 873-881, Oct. 2010.
Fluhr et al., "Development and Validation of the Electron Microscopy Isotropy (EMI) Score: Surface Isotropy as a Marker for Epidermal Maturation," Journal of Investigative Dermatology, vol. 132, Suppl. 2, p. S81, Sep. 2012.
Fluhr et al., "Skin Physiology and surface isotropy investigations in young children of different age groups compared to adults," Journal of the American Academy of Dermatology, vol. 68, No. 4, p. AB177, Apr. 2013.
Fluhr et al., "Functional skin adaptation in infancy—almost complete by not fully competent," Experimental Dermatology, vol. 19, No. 6, pp. 483-492, Jun. 2010.
Rawlings, "Recent advances in skin 'barrier' research," The Journal of Pharmacy and Pharmacology, pp. 671-677, Jun. 2010.
Harding et al., "Dry skin, moisturization and corneodesmolysis," International Journal of Cosmetic Science, vol. 22, No. 1, pp. 21-52, Feb. 2000.
International Search Report issued in application No. PCT/EP2014/068722 dated Nov. 18, 2014.
Agache, Pierre "Stratum Corneum Histophysiology," in "Measuring the Skin" Springer, 2004, pp. 95-100.
Caubet et al., "A new amyloidosis caused by fibrillar aggregates of mutated corneodesmosin," The FASEB Journal, vol. 24, No. 9, 2010, pp. 3416-3426.
Cheng et al., "In Vivo Function of Desmosomes," The Journal of Dermatology, vol. 31, 2004, pp. 171-187.
Extended European Search Report issued in corresponding application No. 13182839.4 dated Oct. 31, 2013.
Fluhr et al., "Development and Validation of the Electron Microscopy Isotropy (EMI) Score: Surface Isotropy as a Marker for Epidermal Maturation," Journal of Investigative Dermatology, 2012, S81.

(Continued)

*Primary Examiner* — Lisa V Cook
(74) *Attorney, Agent, or Firm* — Potomac Law Group, PLLC

(57) ABSTRACT

A method for determining whether the skin surface of a subject is mature/immature in its organization/function, by taking a skin sample and determining the corneodesmosome distribution within the *stratum corneum* of the sample by an immunoelectron microscopy method.

4 Claims, 2 Drawing Sheets

(56) References Cited

PUBLICATIONS

Figure 1:
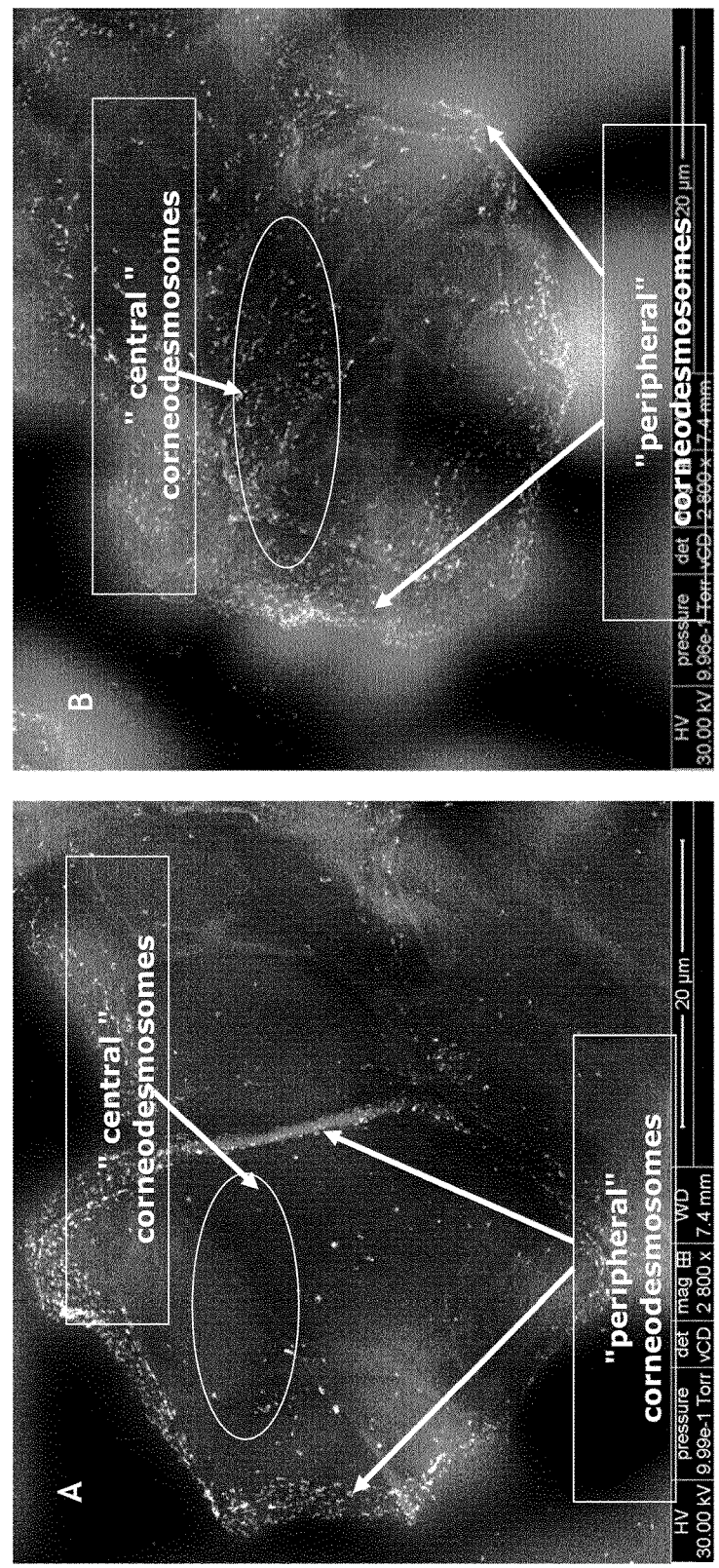

Fluhr et al., "Functional Consequences of a Neutral pH in Neonatal Rat Stratum Corneum," The Society for Investigative Dermatology, Inc., vol. 123, 2004, pp. 140-151.

Fluhr et al., "Functional skin adaptation in infancy—almost complete but not fully competent," Experimental Dermatology, vol. 19, 2010, pp. 483-492.

Fluhr et al., "Infant epidermal skin physiology: adaptation after birth" British Journal of Dermatology, vol. 166, No. 3, 2012, pp. 483-490.

Fluhr et al., "Skin physiology and surface isotropy investigations in young children of different age groups compared to adults," J Am Acad Dermatol, Apr. 2013, p. AB177.

Fluhr et al., "Topical Peroxisome Proliferator Activated Receipt Activators Accelerate Postnatal Stratum Corneum Acidification," The Society for Investigative Dermatology, vol. 129, 2008, pp. 365-374.

Garrod et al., "Desmosomal adhesion: structural basis, molecular mechanism and regulation (Review)," Molecular Membrane Biology, vol. 19, 2002, pp. 81-94.

Haftek et al., "Corneodesmosomes: Pivotal Actors in the Stratum Corneum Cohesion and Desquamation," in "Skin Barrier," Elias P-M, Feingold K-R Ed, Marcel Dekker, Inc., 2004, pp. 171-189.

Harding et al., "Dry skin, moisturization and corneodesmolysis," International Journal of Cosmetic Science, vol. 22, 2000, pp. 21-52.

Harding et al., "The cornified cell envelope: an important marker of stratum corneum maturation in healthy and dry skin," International Journal of Cosmetic Science, vol. 25, 2003, pp. 157-167.

Igawa et al., "Aberrant distribution patterns of cornodesmosomal components of tape-stripped corneocytes in atopic dermatitis and related skin conditions (ichthyosis vulgaris, Netherton syndrome and peeling skin syndrome type B)" Journal of Dermatological Science, vol. 72, 2013, pp. 54-60.

Igawa et al., "Tight junctions in the stratum corneum explain spatial differences in corneodesmosome degradation," Experimental Dermatology, vol. 20, No. 1, 2011, pp. 53-57.

International Search Report issued in corresponding application No. PCT/EP2014/068722 dated Nov. 18, 2014.

Jonca et al., "Corneodesmosin: Structure, Function and Involvement in Pathophysiology," The Open Dermatology Journal, vol. 4, 2010, pp. 36-45.

Jonca et al., "Corneodesmosomes and corneodesmosin: from the *Stratum corneum* cohesion to the pathophysiology of genodermatoses," Eur J Dematol, vol. 21 (Suppl. 2), 2011, pp. 35-42.

Lundstrom et al., "Evidence for a role of corneodesmosin, a protein which may serve to modify desmosomes during cornification, in stratum corneum cell cohesion and desquamation," Arch Dermatol Res, vol. 286, 1994, pp. 369-375.

Matsumoto et al., "Targeted deletion of the murine *Corneodesmosin* gene delineates its essential role in skin and hair physiology" PNAS, vol. 105, No. 18, 2008, pp. 6720-6724.

Naoe et al., "Bidimensional analysis of desmoglein 1 distribution on the outermost corneocytes provides the structural and functional information of the stratum corneum," Journal of Dermatological Science, vol. 57, 2010, pp. 192-198.

Oji et al., "Loss of Corneodesmosin Leads to Severe Skin Barrier Defect, Pruritus, and Atopy: Unraveling the Peeling Skin Disease," The American Journal of Human Genetics, vol. 87, 2010, pp. 274-281.

Oyama et al., "New non-invasive method for evaluation of the stratum corneum structure in diseases with abnormal keratinization by immunofluorescence microscopy of desmoglein 1 distribution in tape-stripped samples," Journal of Dermatology, vol. 37, 2010, pp. 873-881.

Rawlings, Anthony, "Recent advances in skin 'barrier' research," Journal of Pharmacy and Pharmacology, vol. 62, 2010, pp. 671-677.

Schwarz et al., "Desmosomes and Hemidesmosomes: Constitutive Molecular Components," Annu. Rev. Cell Biol., vol. 6, 1990, pp. 461-491.

Simon et al., "Characterization and Purification of Human Corneodesmosin, an Epidermal Basic Glycoprotein Associated with Corneocyte-specific Modified Desmosomes," The Journal of Biological Chemistry, vol. 272, No. 50, 1997, pp. 31770-31776.

Simon et al., "Persistence of Both Peripheral and Non-Peripheral Corneodesmosomes in the Upper Stratum Corneum of Winter Xerosis Skin Versus only Peripheral in Normal Skin," vol. 116, 2001, pp. 23-30.

Simon et al., "Refined Characterization of Corneodesmosin Proteolysis during Terminal Differentiation of Human Epidermis and Its Relationship to Desquamation," vol. 276, No. 23, 2001, pp. 20292-20299.

Stamatas et al., "Infant skin physiology and development during the first years of life: a review of recent findings based on in vivo studies," vol. 33, 2011, pp. 17-24.

* cited by examiner

CORNEODESOMOSOMES AND BARRIER FUNCTION MATURATION

The skin is the largest organ of the human body and it has several functions. The most important is to protect the body against external influences.

With a surface area of about 2 m$^2$, the skin is the largest organ of the human body (about 16% of total body weight). Its principal function is to establish a protective barrier against environmental insults while allowing some exchanges between the interior medium and the external medium. It is the seat of many metabolic processes modulated by the physiological conditions of the organism and the conditions of the environment. The skin is made of two joined layers: the epidermis and the dermis, with which the subcutaneous tissues are associated.

The epidermis constitutes the outermost structure of the skin. Its principal role is the protection of the body: it ensures the impermeability of the skin and its resistance. This tissue is in particular made up of a pluristratified epithelium, called the interfollicular epithelium, whose role is notably to provide a barrier function with respect to the environment. The interfollicular epithelium consists of four distinct cellular layers, a basal layer (*stratum basalis*), a horny layer (*stratum spinosum*), a granular layer (*stratum granulosum*) and a corneal layer (*stratum corneum*).

In particular the barrier function of skin, which protects the body by preventing fluid loss and the penetration of undesirable substances, is primarily fulfilled by the *stratum corneum*. This layer is composed of specific cells, corneocytes, which are completely flat cells, without a nucleus or cytoplasmic organelles, and are the result of the terminal phase of keratinocyte differentiation. The *stratum corneum* is more particularly divided into two distinct layers, one where the corneocytes are still connected to each other via corneodesmosomes, and another where, under the action of specific enzymes, the corneodesmosomes break down, enabling the corneocytes to become detached, a process called desquamation (Haftek et al., in "*Measuring the Skin*", P. Agache a P. Humbert Eds, Springer, 2004; Igawa et al., *Exp Dermatol.*, 20(1): 53-57, 2011; Jonca, *Eur J Dermatol.*, 21(Suppl 2): 35-42, 2011). This process takes part in the continuous renewal of the epidermis This is an extremely important factor to consider when designing cosmetics, since it is the *stratum corneum* that interfaces with cosmetic products like creams and lotions.

Over the last decade, knowledge on newborn skin physiology has evolved. It is now clear that postnatal life is a time period of active functional maturation and cutaneous adaptation to the dry extra-uterine environment. Different environmental factors (for instance, dry and cold climate, diapers and cosmetic care procedures) influence the postnatal development of skin functional parameters such as *stratum corneum* hydration and the permeability barrier especially in premature infants (see e.g. Stamatas et al., *Int J Cosmet Sci.*, 33(1): 17-24, 2011). In particular, corneodesmosomes are important for the barrier function. For example, corneodesmosin, the major protein component of the corneodesmosomes, is necessary for maintaining the integrity and water impermeability of the postnatal epidermis (Matsumoto et al., *Proc Natl Acad Sci*, 105(18): 6720-6724, 2008; Oji et al., *Am J Hum Genet*, 87(2):274-81, 2010; Jonca, *Eur J Dermatol.*, 21(Suppl 2): 35-42, 2011; Simon et al., *J Invest Dermatol*, 116: 23-30, 2011).

In a previous study (Fluhr et al., *Br J Dermatol*, 166(3): 483-90, 2012), the present inventors showed that the moisture and water content of the *stratum corneum* are lower at birth (infants 1 to 15 days), while the rate of natural moisturizing factor (NMF) is maximum. This rate then decreases while the hydration stabilizes. The authors hypothesize that the reduced acidification and lower hydration of the skin could activate regulatory mechanisms of compensation (including a significant production of NMF), which enables the newborn to adapt to his new environment.

In order to obtain a thorough assessment of the barrier function, one has to rely on measuring parameters such as NMF, which only give a global assessment of the barrier function of the epidermis. However, these parameters do not give any information on the spatial organization of the barrier function within the skin structure.

There is thus still a need for the development of new tools for assessing organization of the barrier function of the skin.

DESCRIPTION

The present inventors have shown that the level of maturation of the skin, and thus of its organization/function, can easily be determined by assessing the distribution of corneodesmosomes in the *stratum corneum*.

In order to elucidate the main cutaneous physiological functions in newborns, a clinical study was performed. This study aimed at investigating non-invasively skin surface maturation, by characterizing infant skin in comparison to different children age groups and adult's skin.

The present invention thus relates to a method for determining the degree of maturation of the skin surface of a subject. In particular, the present inventors have shown that the degree of skin maturation is closely related to the distribution of corneodesmosomes in the *stratum corneum*, as shown by the localization of the corneodesmosomes within the *stratum corneum* of subjects of different ages. In fact, the fraction of corneocytes displaying corneodesmosomes in the central region of the cell surface varies with the age of the subject, and is a convenient marker of the level of maturation of the skin surface of the said subject.

The method of the invention thus enables the characterization of the skin surface from birth and the monitoring of its evolution over time. A "child" means according to the invention an individual whose age is less than 16 years. In particular, are included within the category of children according to the invention, neonates of 1 to 15 days, infants of 5/6 weeks, infants of 6 months±1 month, infants of 1 to 2 years, and infants of 4 to 5 years. A "neonate" as used herein, may as well be born at term as being premature. To avoid ambiguity, the term "child" used in this application without further explanation must be understood in its broadest sense, that is to say, as referring to a person under 16 years. An "adult" within the meaning of the present invention is a person who is not a child, i.e. a person aged over 16 years.

Preferably, the method of the invention can be used regardless of ethnicity or geographical skin, or phototype of it. It may well be of Caucasian, African, Asian, South American, Melanesian or any other origin; it can present a phototype I, II, III, IV, V or VI, without thereby affecting the invention. The method of the invention is indeed directed to the determination of skin surface maturation, regardless of the skin type, but depending only on donor age.

The present invention thus relates to a method for determining the degree of maturation of the skin surface of a subject, said method comprising a step of assessing the distribution of corneodesmosomes within the *stratum corneum*.

In a first embodiment, the invention provides a method for determining whether the skin surface of a subject is mature/immature in its organization/function, said method comprising the steps of:
a) taking a skin sample of the said subject; and
b) determining the corneodesmosome distribution within the said sample.

A "skin sample" according to the invention comprises any sample containing skin cells. Advantageously, the said skin sample is obtained from the surface of the skin by stripping the said surface. Various devices useful for this purpose are commercially available, such as, e.g. the D-SQUAME® Skin Sampling Discs (CuDerm).

By "distribution of corneodesmosomes", it is herein referred to the localization of the corneodesmosomes on the cell surface of the corneocytes. For example, the corneodesmosomes could be mostly located between adjacent corneocytes in the same cell layer. Such corneodesmosomes would appear to be located at the periphery of the corneocytes and are thus referred herein to as being "peripheral" or "lateral". For the purposes of the present invention, these two terms should be construed similarly and should be understood as carrying the same meaning. Alternatively, the corneodesmosomes could join adjacent corneocytes between two cell layers, i.e. a top cell layer and a bottom cell layer. Such corneodesmosomes would not appear to be located at the edge of the cells, but rather in a central location. Such corneodesmosomes are herein referred to as "non-peripheral" or "central", these terms being synonymous according to the present invention.

In addition, the person of skills in the art will realize that it is possible to quantify the corneocytes of the sample presenting a certain type of corneodesmosome localization. For example, it may be advantageous to determine the fraction of corneocytes displaying non-peripheral corneodesmosomes. Thus, the method of the invention may comprise a further step of determining the fraction of corneocytes in the sample displaying non-peripheral corneodesmosomes.

By "corneodesmosomes", it is herein referred to intercellular junctions within the *stratum corneum* which are derived from desmosomes. Whereas desmosomes comprise a characteristic tri-lamellar core, corneodesmosomes contain a homogenous electron-dense intercellular portion.

Preferably, the corneodesmosomes of the invention are junctions between corneocytes. "Corneocytes", as used herein, are terminally differentiated keratinocytes and, as such, compose most if not all of the *stratum corneum*.

More preferably, the corneodesmosomes are protein structures forming cell-cell junctions between the corneocytes of the *stratum corneum*.

Several proteins have been identified as components of the desmosomes which are also present in corneodesmosomes. For example, major transmembrane corneodesmosomal proteins have been identified as desmoglein 1 (Dsg1), plakoglobin and desmocollin 1, and heterophilic interactions between these glycoproteins constitute desmosome-mediated cell-cell adhesion (see e.g. Schwarz et al., Ann Rev Cell Biol, 6: 461-491, 1990; Garrod et al., Mol Membr Biol, 19: 81-94, 2002; Cheng a Koch P J, J Dermatol, 31: 171-187, 2004).

Another protein which is a component of the corneodesmosomes is corneodesmosin (CDSN) (Simon et al., *J Biol Chem*, 272: 31770-31776, 1997; Simon et al., J Biol Chem, 276: 20292-20299, 2001). Corneodesmosin is a specific marker for corneodesmosomes, since it is the only protein specifically localized in the extracellular part of corneodesmosomes (Jonca et al., *The Open Dermatology Journal*, 4: 36-45, 2010; Jonca et al., *Eur J Dermatol*, 21(Suppl 2): 35-42, 2011). During maturation of the cornified layers, the protein undergoes a series of cleavages, which are thought to be required for desquamation and thus contribute to the normal turnover of the *stratum corneum* (Lundström et al., *Arch Dermatol Res,* 286(7): 369-375, 1994; Haftek et al., in "Skin Barrier", Elias P-M, Feingold K-R Ed, Marcel Dekker, Inc., NEW YORK, 2005). The phenotypes associated corneodesmosin mutations indicate that this protein is crucial for normal skin function (Agache, in "*Measuring the Skin*", P. Agache a P. Humbert Eds, Springer, 2004; Matsumoto et al., *Proc Natl Acad Sci,* 105(18): 6720-6724, 2008; Caubet et al., *FASEB J.,* 24(9): 3416-3426, 2010) including normal epithelial barrier function (Oji et al., *Am J Hum Genet,* 87(2):274-81, 2010).

By corneodesmosin, it is herein referred to the human protein having the sequence represented by NP_001255, and encoded by the CDSN gene, which has the sequence represented by NM_001264.

Because corneodesmosin is the sole protein which is specific of corneodesmosomes, its distribution accurately reflects the distribution of corneodesmosomes.

By "distribution of corneodesmosin", it is herein referred to the localization of the said protein. Preferably, the said protein is localized onto the cell surface of the corneocytes.

In a preferred embodiment, the corneodesmosomes of the invention thus comprise at least one protein which is corneodesmosin. According to this embodiment, the assessment of the distribution of corneodesmosomes within the *stratum corneum* according to the invention is thus performed by assessing the distribution of corneodesmosin.

Thus, according to this embodiment, the present invention relates to a method of determining whether the skin surface of a subject is mature or immature in its organisation/function, said method comprising the steps of:
a) taking a skin sample (A) of the said subject; and
b) determining the distribution of corneodesmosin within the sample.

The present inventors have shown that corneodesmosin distributed mainly on the lateral rims of the flattened cells, indicating the presence of corneodesmosomes between adjacent cells. However, in children of 1 year and older, corneodesmosin molecules can also be observed in a central cell plateau, which corresponds to the remnant of the attachments of the corneocytes to the underlying cells. Such a distribution is similar to the organization of the adult human *stratum corneum*, indicating that maturity of the *stratum corneum* is reached at 1 year.

In order to improve the specificity of determination of the distribution of corneodesmosin, it may be advantageous to quantify the fraction of corneocytes displaying central corneodesmosomes. The clinical study conducted by the inventors showed that this fraction increases at least 5 times between an age of 5/6 weeks and adulthood. Importantly, the maximal value for this fraction is reached in children who are 1 year old.

On this basis, the inventors were able to distinguish two classes of skin surface maturation in relation to the age of the children:
intermediate maturity: ≥5/6 weeks to 1 years; and
maturity: ≥1 years.

These findings confirm results previously obtained by the present inventors in a different clinical study (see PCT application No. xxx), wherein maturity of the skin surface was found to be reached at 1-2 years (note that the difference stems from a slight difference of the cohort age composition).

In a preferred embodiment, the method of the invention comprises the steps of:
a) taking a skin sample (A) of the said subject; and
b) determining the distribution of corneodesmosin within the sample, wherein the determination of the distribution of corneodesmosin within the sample involves determining the fraction of corneocytes displaying central corneodesmosomes.

It is particularly advantageous to use an antibody specific for the human corneodesmosin to determine the corneodesmosin localization: such an antibody enables the skilled person to accurately and unambiguously determine the localization of the said protein, and therefore to precisely assess the distribution of corneodesmosomes.

As used herein, the term "antibody" is used in the broadest sense and may cover a single species of desirable monoclonal antibodies against any of corneodesmosin polypeptides or related peptide fragments thereof and antibody compositions having a specificity to various epitopes thereof, further monovalent or polyvalent antibodies and polyclonal and monoclonal antibodies, and also those which are intact molecules or fragments and derivatives thereof, including $F(ab)_2$, Fab' and Fab fragments, and also chimeric antibodies, hybrid antibodies each having at least two antigen or epitope binding sites, or bispecific recombinant antibodies (e.g., quadromes, triomes, etc.), interspecies hybrid antibodies, anti-idiotypic antibodies and those which have been chemically modified or processed and must be regarded as derivatives of these antibodies and further which may be produced either by adopting cell fusion or hybridoma techniques or antibody engineering or by using synthetical or semisynthetical techniques in known manner, which may be prepared either by the known conventional methods in view of antibody production or by recombinant DNA techniques, and which have neutralizing or binding properties with respect to the target antigen substances or target epitopes described and defined herein. Preferably the inventive antibodies are especially those capable of specifically identifying or distinguishing intact corneodesmosin.

Antibodies directed towards corneodesmosin have been developed and characterized for the last 20 years. For example, such antibodies have been used to characterize corneodesmosin localization and function within the *stratum corneum* of both animals and humans (Matsumoto et al., *Proc Natl Acad Sci*, 105(18): 6720-6724, 2008; Jonca et al., *The Open Dermatology Journal*, 4: 36-45, 2010). Antibodies recognizing corneodesmosin are commercially available from companies such as in R&D Systems, Abnova, or Abcam. For example, the experiments reported in the present examples make use of a monoclonal antibody 6F11 directed against residues 306-356 of corneodesmosin and commercialized by Abnova (Taipei, Taiwan).

The antibody can be present in the form of an immunoconjugate or of a labeled antibody to obtain a detectable/quantifiable signal. When used with suitable labels or other appropriate detectable biomolecules or chemicals, the antibody of the invention is particularly useful for the applications of invention.

Labels for use in immunoassays are generally known to those skilled in the art and include enzymes, radioisotopes, and fluorescent, luminescent and chromogenic substances, including colored particles such as colloidal gold or latex beads. Various types of labels and methods of conjugating the labels to the antibodies of the invention are well known to those skilled in the art, such as the ones set forth below.

Localization of the said protein can be determined by a variety of techniques, all of which are well known to the person of skills in the art. Localization can be effectively demonstrated with fluorescence microscopy-based techniques, electron microscopy methods, or cellular fractionation procedures. In a preferred embodiment, the localization of corneodesmosin is determined by a method selected from the group consisting of fluorescence microscopy-based techniques, electron microscopy methods and cellular fractionation procedures.

In particular, the localization of corneodesmosomes can be determined using any of the various methods of skin imaging known to the person of skills in the art. Such methods include, in particular, all the techniques enabling the person of skills in the art to observe and distinguish the junctions between the cells of the *stratum corneum*. For example, the skilled person can use any of the microscopy techniques commonly used in the laboratory. These techniques include, for example, methods of optical microscopy, such as conventional light microscopy, fluorescence microscopy, confocal/multiphoton microscopy and stimulated emission depletion; scanning probe microscopy, including scanning tunneling microscopy (STM), atomic force microscopy (AFM), near-field scanning optical microscopy and others; and electronic microscopy.

Preferably, corneodesmosin is detected with the said labeled antibodies in the sample of step a) by immunochemistry.

As used herein, "immunohistochemistry" or IHC refers to the process of detecting antigens (e.g., proteins) in cells of a tissue section by exploiting the principle of antibodies binding specifically to antigens in biological tissues. This process relies on contacting the sample of step a) with the said labeled antibodies and detecting the resulting interaction of the antibodies and corneodesmosin by a microscopy-based technique.

Visualizing the interaction between the antibody and corneodesmosin can be accomplished in a number of ways. In the most common instance, an antibody is conjugated to an enzyme, such as peroxidase, that can catalyze a color-producing reaction. Alternatively, the interaction is detected by immunofluorescence.

"Immunofluorescence", as used herein, refers to an antigen-antibody reaction where the antibodies are tagged (labeled) with a fluorescent dye and the antigen-antibody complex is visualized using ultra-violet (fluorescent) microscope.

According to the invention, immunofluorescence comprises direct immunofluorescence and indirect immunofluorescence. In direct immunofluorescence, an antibody directly labeled using an enzyme or a fluorophore is used to detect corneodesmosin. In indirect immunofluorescence, a primary antibody, specific for corneodesmosin, is recognized by a high affinity binding partner, which can be a secondary antibody, which is linked to a fluorophore.

Fluorochromes are dyes that absorb ultra-violet rays and emit visible light. This process is called fluorescence. Commonly used fluorochromes are acridine orange, rhodamine, lissamine and calcofluor white. However, these fluorochromes are used for general fluorescence. When fluorescein (FITC) is excited by a blue (wavelength 488 nm) light, it will emit a green (520 nm) colour. Phycoerythrin (PE) emits an orange (570 nm) colour. The fluorochromes commonly used in immunofluorescence are fluorescein isothiocyanate (green) and tetramethyl rhodamine isothiocyanate (red).

Although immunofluorescence can provide a quick and easy assessment of the distribution of corneodesmosin, it just gives an overview of the said distribution. It cannot provide the same level of details and information as methods such as immunoelectron microscopy. Thus, more preferably, corneodesmosin is detected with the said labeled antibodies in the sample of step a) by immunoelectron microscopy.

"Immunoelectron microscopy" as used herein refers to a technique wherein the binding of an antibody to an antigen present in a sample of a subject, e.g. corneodesmosin, is detected by electron microscopy. Immunoelectron microscopy is thus a tool to reveal the relations of various cellular constituents of known function to subcellular organelles or parts of them, thereby providing information about organizational and functional principles of cellular compartments and subcompartments. Indeed, while conventional electron microscopy provides no information about specific molecules, immunoelectron microscopy helps to connect a visible structure with a specific in situ localization and distribution of molecules at a high resolution. In the present case, immunoelectron microscopy enables the skilled person to observe the localization of corneodesmosin in corneodesmosomes in between corneocytes, and thus to accurately determine the localization of said corneodesmosomes.

Thus, according to this embodiment, the present invention relates to a method of determining whether the skin surface of a subject is mature or immature in its organization/function, said method comprising the steps of:
a) taking a skin sample (A) of the said subject;
b) performing immunoelectronmicroscopy on the said sample with an antibody directed against corneodesmosin and
c) determining the localization of corneodesmosin.

As explained above, it is advantageous to quantify the fraction of corneocytes displaying central corneodesmosomes in order to accurately assess the distribution of corneodesmosin.

In a preferred embodiment, the method of the invention thus comprises the steps of:
a) taking a skin sample (A) of the said subject;
b) performing immunoelectronmicroscopy on the said sample with an antibody directed against corneodesmosin
c) determining the localization of corneodesmosin and
d) determining the fraction of corneocytes displaying central corneodesmosomes.

As known to the person of skills in the art, the success of immunolabeling at ultrastructural level depends on various factors, including the initial quantity and quality of antigens, and the preservation of the cell ultrastructure, to be able to finally achieve an accurate localization of the antigen within the cell. Therefore, it is necessary to attain a correct balance between antigen preservation and a good morphology at the ultrastructural level.

In particular, fixation is one of the most important steps in sample preparation. By "fixation" or "chemical fixation", it is herein referred to the process of inducing the fast arrest of biological activities and the stabilization of subcellular components with a minimal distortion of the cellular structures. Chemical fixation allows biological samples to be prepared for subsequent procedures. Chemical fixation is usually carried out by treating the sample with formaldehyde, glutaraldehyde or a mix thereof. The present inventors have observed that no fixation is required when the detection of the binding of the antibody to the sample is performed by scanning electron microscopy.

Immunoelectron microscopy can be performed by different techniques such as e.g. pre-embed labeling, post-embed labeling, or cryo-sectioning without embedding. "Pre-embed labeling" as used herein refers to a technique wherein the cells or tissue is labeled with antibodies before it is embedding in a resin. In the "post-embed labeling" method, thin sections of cells are labeled with the antibody after they are fixed and embedded in resin. The "cryo-sectioning" method comprises a step of freezing the samples without embedding prior to ultra-thin sectioning. Preferably, pre-embed labeling is used of visualizing superficial antigens, i.e. antigens located at the surface of cells, such as corneodesmosin.

The inventors have shown that samples obtained by stripping the surface of the skin can be incubated directly with the antibody specific for corneodesmosin, i.e. without any priori fixation or treatment of the sample, as exemplified in the experimental section herein.

In order to facilitate the detection of the said antibody binding to corneodesmosin, it is advantageous that the said antibody is labeled.

Hence, in a preferred embodiment, the method of the present invention comprises the steps of:
a) taking a skin sample (A) of the said subject;
b) contacting the said sample with a labeled antibody directed against corneodesmosin, and
c) determining the localization of corneodesmosin.

In a further preferred embodiment, the said method comprises the steps of:
a) taking a skin sample (A) of the said subject;
b) contacting the said sample with a labeled antibody directed against corneodesmosin,
c) determining the localization of corneodesmosin, and
d) determining the fraction of corneocytes displaying central corneodesmosomes.

Preferably, the said antibody is labeled with a label which can be detected by electron microscopy. Such a label is more preferably an electron dense marker that distinguishes it from other cellular components, e.g. an enzymatic marker such as horseradish peroxidase or gold particle. Still more preferably, the antibody of the invention is labeled with gold particles; most preferably, with colloidal gold particles. Such particles have usually diameters ranging from 5 to 40 nm; most often, from 5 to 25 nm. Ultrasmall gold ($\leq 1.0$ nm) have been recently developed, thus providing a marker system with a greater labeling sensitivity. These particles are less prone to steric hindrance and able to penetrate better, even without pretreatment with detergent. Preferably, the antibody of the invention is labeled with ultrasmall gold particles.

Methods for labeling an antibody with colloidal gold particles are well known in the art and need not be detailed herein. Immunogold labeling can be done in one of several ways. In a first embodiment, the colloidal gold particles are conjugated directly to the antibody being used. In another embodiment, the labeling is an indirect method whereby the sample is first incubated in the antibody of interest. Next the sample is exposed to a secondary antibody that reacts to the first antibody.

This secondary antibody is conjugated to a colloidal gold particle which because of its electron density allows one to visualize where in the cell the primary antibody (and by implication corneodesmosin) is localized. According to a preferred embodiment of the invention, the primary antibody, i.e. the antibody recognizing the corneodesmosin protein, is directly labeled with a colloidal gold particle.

In addition, the ultrastructural detection of the antigens can be significantly improved by coupling immunogold labeling with the silver enhancement method. During silver-enhancement, the colloidal gold serves as a nucleation site for the deposition of metallic silver. Samples stained with colloidal gold are "developed" by this autometallographic procedure to give black staining which can be seen in the light microscope. The enhancing solutions are physical developers that contain both silver ions and a reducing agent, buffered to an acid pH. The silver-enhancement method is particularly advantageous for enlarging small-diameter gold particles for visualization by scanning electron microscopy.

Thus, in another preferred embodiment, the immunoelectron microscopy of the invention is performed with a primary antibody, i.e. the antibody recognizing the corneodesmosin protein, directly labeled with a colloidal gold particle, preferably an ultrasmall gold particle, and comprises a step of silver enhancement.

Electronic microscopy techniques suitable for the method of the invention comprise such techniques as e.g. transmission electron microscopy (TEM), scanning transmission electron microscopy (STEM), focus ion beam microscopy (FIB) and scanning electron microscopy (SEM). Preferably, the localization of corneodesmosomes is determined using an electron microscopy technique.

According to this preferred embodiment, the present invention relates to a method of determining whether the skin surface of a subject is mature or immature in its organization/function, said method comprising the steps of:
a) taking a skin sample (A) of the said subject;
b) contacting the said sample with a labeled antibody directed against corneodesmosin,
c) detecting the labeled antibody bound to the sample by electron microscopy, and
d) determining the localization of corneodesmosin.

In a further preferred embodiment, the said method comprises the steps of:
a) taking a skin sample (A) of the said subject;
b) contacting the said sample with a labeled antibody directed against corneodesmosin,
c) detecting the labeled antibody bound to the sample by electron microscopy,
d) determining the localization of corneodesmosin, and
e) determining the fraction of corneocytes displaying central corneodesmosomes.

Scanning electron microscopy (SEM) represents a very precise method for direct analysis of the microstructure of the outermost skin layers and *stratum corneum* in particular. With its resolution and possible magnification from ×100 up to ×100.000, it enables a high quality three-dimensional picture of skin surface topography and ultrastructure. In addition, as explained above, no prior fixation of the sample is required when the immunoelectron microscopy involves using scanning electron microscopy. More preferably, the said corneodesmosomes distribution is determined by performing immunoelectron microscopy involving scanning electron microscopy.

The corneodesmosome distribution of the said skin sample can be determined to a reference obtained from the compilation of previous experimental results. Indeed, as shown by the present inventors, it is clear that the corneodesmosome distribution changes with age. For example, an immature skin surface shows no corneocytes displaying central corneodesmosomes, whereas the presence of corneodesmosomes in the central region of the cells is associated with a mature skin surface.

Alternatively, it is possible to compare the corneodesmosome distribution of the skin sample of the invention with the corneodesmosome distribution of a skin sample from a reference subject. It will be easily understood that, if the said skin sample shows the same corneodesmosome distribution as the reference skin, the said skin thus displays the same level of maturity as the said reference skin. For example, if the said skin sample shows the same corneodesmosome distribution as the reference skin and the said reference skin is mature, the said skin is also mature, whereas an identical corneodesmosome distribution with a reference immature skin means that the said skin is immature.

By "reference subject", it is herein meant a subject whose age is known. Preferably, a reference subject is a newborn of 1 to 15 days, an infant of 5/6 weeks, an infant of 6 months±1 month, an infant of 1 to 2 years, an infant of 4 to 5 years, or an adult of over 16 years.

It will be clear to those skilled in the art that the invention has the advantage of enabling the easy isolation and characterization of active agents, cosmetic raw materials and/or cosmetic formulations. In particular, tolerance, skin penetration and efficiency of an active agent can easily be checked with the method of the invention.

More precisely, the present invention enables to verify that these agents are suited to the maturation stage of the skin surface of a specific class age. In particular, it is important to isolate agents which will reinforce or maintain the barrier organization/function of an immature or moderately mature skin surface, or to maintain the barrier organization/function of a mature skin. For example, it may desirable to isolate agents which will greatly improve the maturation level of the skin in newborns, while agents respecting the skin surface maturation may be convenient for infants of above 1 year.

In another aspect, the invention thus enables the isolation of active agents having an effect on the skin, particularly on the skin of children, and more particularly on the skin of newborns of 1 to 15 days, infants of 5/6 weeks, infants of 6 months±1 month, infants of 1 to 2 years, and infants of 4 to 5 years. Specifically, the identification of the maturation stage of the skin surface according to the method of the invention enables the identification of active agents reinforcing or maintaining the barrier function of the said skin.

The invention therefore also relates to a method for identifying an active agent for the preparation of a cosmetic, pharmaceutical, food and/or nutraceutical composition, said method comprising the steps of:
a) obtaining at least one sample (A) of skin cells of a subject;
b) contacting a candidate active agent with the sample (A);
c) determining the level of maturation of the skin surface of the sample (A) by the method of the invention;
d) determining the level of maturation of the skin surface in a control sample;
e) comparing the level of expression of step c) and the level of expression of step d), and
f) determining whether said candidate active agent is an active agent for the preparation of a cosmetic, pharmaceutical, food and/or nutraceutical composition of the skin of a subject.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years, or an infant of 4 to 5 years.

The control sample according to the invention is a sample that has not been in contact with the candidate active agent, thus allowing a significant comparison between the skin surface maturation level of step c) and that of step d). For example, the sample (A) that has not been contacted with the candidate can be used as a control. In this case, the maturation of the skin surface is evaluated in the sample (A) before and after being brought into contact with the candidate active agent.

The candidate is an active agent for preparing a cosmetic composition for the skin, if said active agent maintains or improves the maturation level of the skin surface.

Preferably, the active agent of the invention is capable of restoring the normal level of skin maturation. By "normal level", it is herein referred to the level of maturation of the skin surface commonly observed in a population of healthy subjects of the same age as the subject. In other words, the surface of the treated skin shows a distribution of corneodesmosomes which is the same as the one observed in a population of healthy subjects of the same age. In still other words, the corneodesmosome distribution is the same as the one observed in a population of healthy subjects of the same age. More preferably, the surface of the treated skin shows a corneodesmosome distribution and a topography which are the same as the ones observed in a population of healthy subjects of the same age. In yet other words, the corneodesmosome distribution and the developed surface are the same as the ones observed in a population of healthy subjects of the same age.

Alternatively, the active agent of the invention is capable of leading to an improved level of skin maturation. By "improved level", it is herein referred to the level of maturation of the skin surface commonly observed in a population of healthy subjects of the same age as the subject. In other words, the surface of the treated skin shows a distribution of corneodesmosomes improved when compared to the one observed in a population of healthy subjects of the same age. In still other words, the fraction of corneocytes displaying central corneodesmosomes is higher than the one observed in a population of healthy subjects of the same age.

In another aspect, the invention enables the isolation of raw materials, which can be used in the development of formulations for the skin, particularly for the skin of the child, and, more particularly, for the skin of newborns of 1 to 15 days, infants of 5/6 weeks, infants of 6 months±1 month, infants of 1 to 2 years, and infants of 4 to 5 years. A formulation of the invention is a preparation obtained by mixing different raw materials, to meet a demand expressed generally in terms of properties. The formulations of the invention can be used in cosmetics, pharmaceutical, food and/or nutraceutical. They can be used in humans or animals, by oral or topical application.

The invention thus enables the identification of raw materials improving tolerance. The determination of the skin maturation level according to the method of the invention allows the identification of raw materials or not modulating the said maturation.

The invention therefore also relates to a method for identifying a raw material that can be used for the preparation of a cosmetic, pharmaceutical, food and/or nutraceutical formulation, said method comprising the steps of:
  a) obtaining at least one skin sample (A) from a subject;
  b) contacting a candidate raw material with the sample (A);
  c) determining the level of maturation of the skin surface of the sample (A) by the method of the invention;
  d) determining the level of maturation of the skin surface of a control sample;
  e) comparing the level of maturation of step c) and the level of maturation of step d), and
  f) determining if said material is a candidate material for the preparation of a cosmetic, pharmaceutical, food and/or nutraceutical formulation.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years, or an infant of 4 to 5 years.

The control sample according to the invention is a sample that has not been in contact with the candidate raw material, thus allowing a significant comparison between the skin surface maturation level of step c) and that of step d). For example, the sample (A) that has not been contacted with the candidate raw material can be used as a control. In this case, the maturation of the skin surface is evaluated in the sample (A) before and after being brought into contact with the candidate raw material.

As explained hereabove, it is important that the agents, raw materials or formulations of the invention are suited to the maturation stage of the skin surface of a specific class age. Thus, in a preferred embodiment, the active agent, raw material, or cosmetic, pharmaceutical, food and/or nutraceutical formulation of the invention accompanies, protects, or restores the maturation of the skin.

It is clear that the invention thus not only enables the isolation and characterization of raw materials that can be used in cosmetic, pharmaceutical, food and/or nutraceutical formulations, but also to test said formulations already made and to identify those that have optimal qualities of tolerance, efficacy, toxicology and skin penetration vis-à-vis a subject's skin, especially a child's skin. In particular, those skilled in the art will understand readily that that the identification of the maturation level of the surface of the skin according to the method of the invention is crucial in determining whether a formulation can be used on the skin of children.

The invention therefore also relates to a method for identifying a cosmetic, pharmaceutical, food and/or nutraceutical formulation for the skin, said method comprising the steps of:
  a) obtaining at least one skin sample (A) of a subject;
  b) contacting a candidate active formulation with the sample (A);
  c) determining the level of maturation of the skin surface of the sample (A) by the method of the invention;
  d) determining the level of maturation of the skin surface in a control sample;
  e) comparing the level of maturation of step c) and the level of maturation of step d), and
  f) determining whether said candidate formulation is a cosmetic, pharmaceutical, food and/or nutraceutical formulation.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years, or an infant of 4 to 5 years.

The control sample according to the invention is a sample that has not been in contact with the candidate formulation, thus allowing a significant comparison between the skin surface maturation level of step c) and that of step d). For example, the sample (A) that has not been contacted with the candidate formulation can be used as a control. In this case, the maturation of the skin surface is evaluated in the sample (A) before and after being brought into contact with the candidate formulation.

In another aspect, the invention relates to a method for assessing the tolerance of a cosmetic, pharmaceutical, food and/or nutraceutical composition, said method comprising the steps of:
- a) obtaining at least one sample (A) of skin cells of a subject;
- b) contacting a candidate active agent with the sample (A);
- c) determining the level of maturation of the skin surface of the sample (A) by the method of the invention;
- d) determining the level of maturation of the skin surface in a control sample;
- e) comparing the level of expression of step c) and the level of expression of step d), and
- f) determining whether said cosmetic, pharmaceutical, food and/or nutraceutical composition of the skin of a subject is tolerated by the skin of the subject.

According to a preferred embodiment, the subject from whom the sample (A) is obtained is a child. Even more preferably, this subject is a newborn of 1 to 15 days, an infant of 5/6 weeks, an infant of 6 months±1 month or an infant of 1 to 2 years.

The control sample according to the invention is a sample that has not been in contact with the candidate active agent, thus allowing a significant comparison between the skin surface maturation level of step c) and that of step d). For example, the sample (A) that has not been contacted with the candidate can be used as a control. In this case, the maturation of the skin surface is evaluated in the sample (A) before and after being brought into contact with the candidate active agent.

According to another aspect of the invention, the level of maturation of the skin surface can be used to characterize skin disorders. Specifically, it is possible to characterize, using said maturation level of the invention, skin diseases affecting newborns, infants, children whose age is between 2 and 16, and/or adults.

By "skin disorder", it is herein referred to all abnormal reactions that can affect the skin of an individual. These conditions affect both the skin itself (that is to say, the epidermis, dermis and/or hypodermis), the pores of the skin, sweat and sebaceous glands attached thereto, hair or nails.

Skin disorders according to the invention result in injuries, which corresponds to a damaged skin or a skin in poor condition. Damaged skin includes such reactive sensitive skin, dry skin, skin damaged by the sun, by radiation, by the cold, by stress or pollution, by an allergy, urticaria, eczema and by other forms of dermatitis such as atopic dermatitis, impetigo, irritative dermatitis, particularly irritant dermatitis of the seat or diaper rash, contact dermatitis, seborrheic dermatitis of the skin and scalp (cradle cap), psoriasis, disease-Lainer Moussous, or through wounds or burns. Skin disorder is therefore meant to include disorders as diverse as herpes, angiomas (including tuberous, subcutaneous or plans), hemangiomas, baby acne, adolescent acne, ichthyoses (e.g. vulgaris, congenital, lamellaris . . . ) etc. A skin disorder can be caused or exacerbated by an external infection example of parasitic, viral, bacterial or fungal. The term "skin disorder" as used herein is also meant to encompass as well the warts, strophulus prurigo, scabies, head lice, or fungal infections. The latter are caused by parasitic fungi proliferation of parasites in the body. The most common fungal infections comprise candidiasis and pityrosporoses, which are caused by yeast overgrowth of the skin.

Such skin disorders can have potentially deleterious effects on the skin barrier function, as is the case for, e.g., dry skin. Such effects would translate into an alteration of the maturation level of the skin surface.

As is also known to the skilled person, some general diseases may also be manifested by symptoms affecting the skin. For example, dermatitis or rash is known to be caused by a great variety of diseases. As explained above, dermatitis may occur with viral infections, such as herpes zoster; fungal infections, such as a yeast infection (*Candida albicans*); bacterial infections, such as impetigo; and sexually transmitted infections (STIs). But it may also occur as a symptom of a more serious disease, such as liver disease, kidney disease, or some types of cancer. Dermatitis may also appear as a side effect to some medicines. A very rare and serious type of generalized red rash called toxic epidermal necrolysis (TEN) may occur after using sulfa drugs and can cause the skin to peel away, leaving large areas of tissue that weep or ooze fluid like a severe burn.

According to this particular embodiment, the invention provides a method of determining if a skin disorder or a general disease affects the maturation of the skin surface, said method comprising the following steps:
- a) obtaining at least one one skin sample (A') of a subject affected by said skin disorder or general disease;
- b) obtaining at least one control skin sample (B) of a healthy subject;
- c) determining the level of maturation of the skin surface of the sample (A') by the method of the invention;
- d) determining the level of maturation of the skin surface of the sample of step b) by the method of the invention;
- e) comparing the level of maturation of step a) and the level of maturation of step b), and
- f) determining whether the level maturation of the skin surface is affected by the said skin disorder or general disease.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years, or an infant of 4 to 5 years.

It will be immediately clear to the person of skills in the art that the effect of a skin disorder on the maturation of the skin surface is immediately advantageous for isolating agents active in treating the said disorder.

The invention therefore also relates to a method for identifying an active agent for treating a particular skin disorder, said method comprising the steps of:
- a) obtaining at least one skin sample (A') from a subject affected by said skin disorder;
- b) contacting a candidate agent with the said sample (A');
- c) determining the level of maturation of the skin surface of the sample (A') by the method of the invention;
- d) determining the level of maturation of the skin surface of at least one control sample;
- e) comparing the level of maturation of step c) and the level of maturation of step d), and
- f) determining if said candidate is an active agent for treating skin disorders.

According to a preferred embodiment, the subject from whom the sample (A) is obtained is a child. Even more preferably, this subject is a newborn of 1 to 15 days, an infant of 5/6 weeks, an infant of 6 months±1 month, an infant of 1 to 2 years, or an infant of 4 to 5 years.

Preferably, the active agent of the invention is capable of restoring the normal level of skin maturation. By "normal level", it is herein referred to the level of maturation of the skin surface commonly observed in a population of healthy subjects of the same age as the subject. In other words, the surface of the treated skin shows a distribution of corneodesmosomes which is the same as the one observed in a population of healthy subjects of the same age. In still other words, the corneodesmosome distribution is the same as the one observed in a population of healthy subjects of the same age. More preferably, the surface of the treated skin shows a corneodesmosome distribution and a topography which are the same as the ones observed in a population of healthy subjects of the same age. In yet other words, the corneodesmosome distribution and the developed surface are the same as the ones observed in a population of healthy subjects of the same age.

Alternatively, the active agent of the invention is capable of leading to an improved level of skin maturation. By "improved level", it is herein referred to the level of maturation of the skin surface commonly observed in a population of healthy subjects of the same age as the subject. In other words, the surface of the treated skin shows a distribution of corneodesmosomes improved when compared to the one observed in a population of healthy subjects of the same age. In still other words, the fraction of corneocytes displaying central corneodesmosomes is higher than the one observed in a population of healthy subjects of the same age.

The examples that follow are merely exemplary of the scope of this invention and content of this disclosure. One skilled in the art can devise and construct numerous modifications to the examples listed below without departing from the scope of this invention.

FIGURES LEGENDS

FIG. 1: Two examples of corneodesmosome remnants visualized with immunogold and silver enhancement (A, B). Secondary electron image of an adult sample. Silver enhancement; ×2,800.

Figure 2:
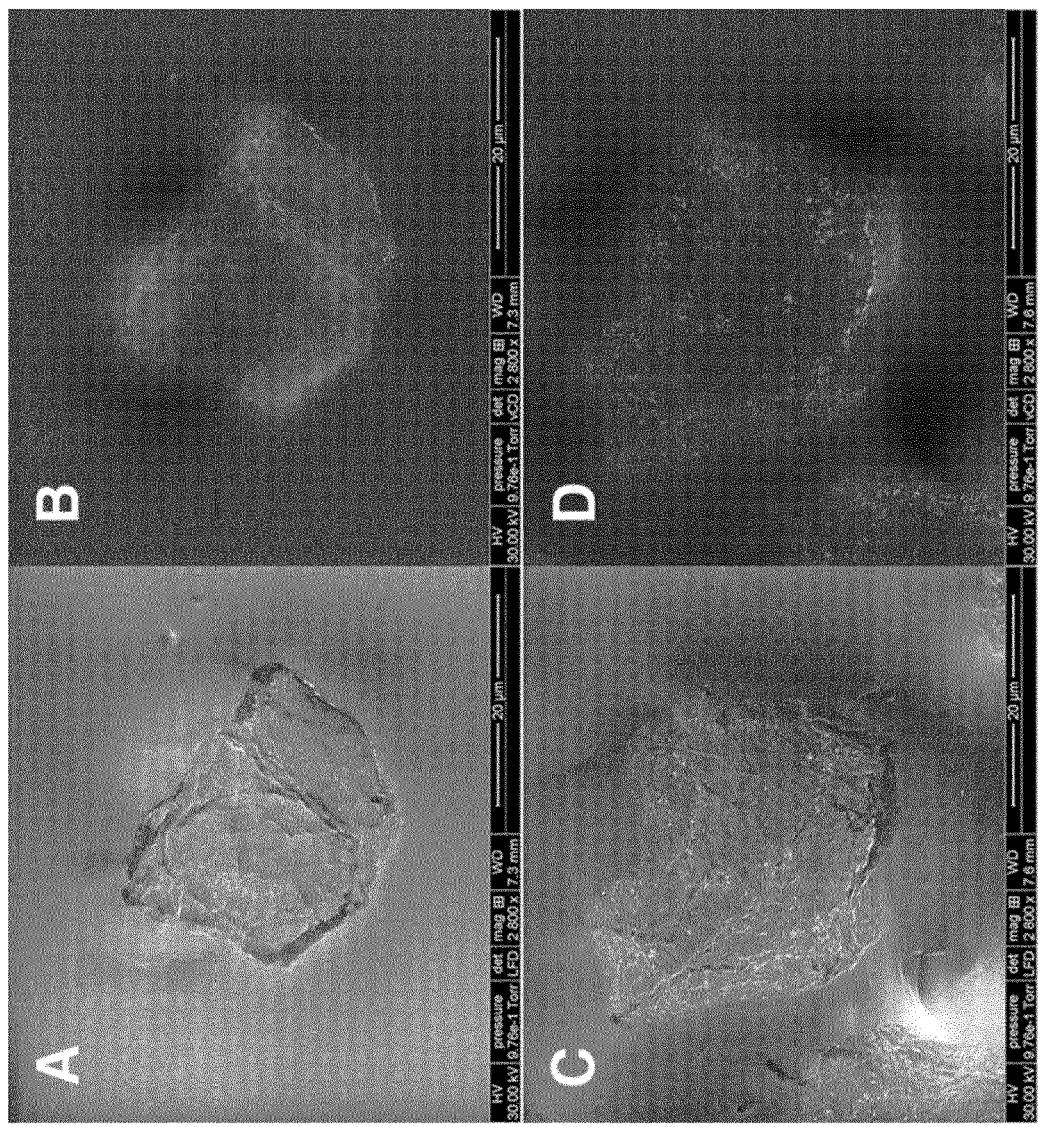

FIG. 2: Examples of corneocytes exhibiting corneodesmosin labelling over the central area, in addition to the peripheral rim. A, B) linear imprint of the peripheral attachment of overlapping underlying cells. C, D) even distribution evoking persistence of the "central" corneodesmosomes. Secondary electron (A, C) and back-scatter (B, D) images of a 4-5 y.o. child's sample. Silver enhancement; ×2,800.

EXAMPLES

Material and Methods

Study Protocol

A detailed description of the enrolled subjects is provided in the Table 1. Whenever possible, adults were recruited among the parents of the younger age groups. Only healthy infants and adults with no present and/or past history of skin disease were included. Topical application of any products on the test sites (volar forearm) was not allowed within the last three days prior to the start and during the study. Taking a short shower was allowed, provided that the test fields were not washed with soap/detergent or with any other skin care product. The study was performed in Berlin, Germany, from the end of January to September 2011, with a recruitment pause during July and August. The selection of subjects was in accordance with the requirements of §§ 40 and 41 of the German Drug Law as well as the recommendations of the Somerset West revision of the Helsinki Declaration (1996) and the ICH-GCP Guideline, as applicable for this study. Subjects and/or parents or legal guardians signed a written informed consent before the start of each study. The studies were approved by the local authorities and by the Freiburg ethics commission international.

The aim of the study was to investigate corneodesmosin distribution by immunocytochemical corneocyte labelling. This part was performed in subjects (both genders) divided in 4 age groups (5 subjects per group) for immunocytochemical investigations. There was no new-born group. All subjects completed the study and there were no dropouts. No adverse events were observed during the study procedures.

Sample Collection

The subjects were acclimatized for at least 30 minutes in an air-conditioned room at 20° C.☐2 and 50%☐10 relative humidity. The test area—volar forearm, was left uncovered from clothing. One 22 mm D-Squame® disc (CuDerm, Dallas, Tex., USA) was applied with a normalized pressure to the volar forearm of every subject for 1 min. The adhesive disc was subsequently peeled off.

Immuno-Electron Microscopy of Corneodesmosome Remnants.

An analysis of corneodesmosomes persisting on the most superficial cells harvested with D-Squames® was performed in 5 subjects randomly chosen from 4 age groups in study B. D-Squames® from the volar forearm were stored in sealed plastic tubes at −80° C. Corneodesmosome remnants were labelled on freshly thawed corneocytes, without previous fixation. Binding sites of monoclonal mouse antibody to recombinant corneodesmosin (306-356 aa) clone 6F11, diluted 1/200 in PBS (90 min. at room temperature; Abnova, Taipei, Tiwan) were revealed with goat anti-mouse IgG conjugated to 1 nm colloidal gold (diluted 1/10; Amersham, Little Chalfont, UK). The immunogold labelling was amplified with silver coating for 10 min. at 18° C. (Silver Enhancement kit; British BioCell International, Cardiff, UK). The controls included fragments incubated with PBS instead of the primary or secondary antibody and subjected to the silver amplification alone. The samples were then partially dehydrated in ethanol (5 min. in 30°, 50°, 70°, and 95°). Observation of the D-Squame® fragments took place in partial vacuum (1 Torr) at 30 kV with Quanta 250 FEG scanning microscope (FEI company, EC) operating at back-scatter and secondary electron detection modes (revealing, respectively, compositional and topographic details). Digital pictures of isolated corneocytes and of non-dissociated cell clusters, taken at magnifications ×1,000 and ×2,800, were used for evaluation of the corneocyte size and corneodesmosome distribution. Over 80 corneocytes per sample were evaluated in 5 samples and in 4 age groups: 5-6 weeks, 1 year, 4-5 years, and 20-35 years. Image J free-access on-line software was used for quantitative studies.

Statistical Analysis

Demographic and background data were summarized by age group using descriptive statistical methods. Occurrence of the corneocytes displaying retained central corneodesmosomes and mean projected area of individual cells within the different age groups were compared using non-parametric Mann-Whitney test.

Results

Immuno-Scanning Electron Microscopy of Corneodesmosome Remnants Indicates Maturation of the Desquamation Process During the First Year after Birth.

Silver-enhanced immunogold labelling specifically localized to the disrupted corneodesmosome structures distributed mainly on the lateral rims of the flattened cells (FIGS. 1 and 2). Variable percentage of corneocytes presented also some labelling at the area of the central plateau (Table 2). Most frequently, these traces were linear and constituted the imprints of attachment to the periphery of the underlying cells, i.e. to the corneocytes that remained at the skin surface after D-Squame® stripping (FIGS. 1 and 2 A, B). In some instances, however, the distribution of disrupted corneodesmosomes was quite even over the central area (FIGS. 1 and 2 C, D). The frequency of occurrence of these cells was recorded, as corneocytes with the preserved "central" corneodesmosomes presented characteristics of the SC *compactum* of adult human epidermis. A striking difference was recorded between the samples collected at 5-6 weeks of age and those from the older groups (Table 2; left column). The adult-like distribution started already from the first year age. The corneocyte measured projected area showed a progressive age-dependent increase (Table 2; right column). Inter-group differences were statistically significant; with notable differences between the 5-6 weeks and adult groups visible already at low magnification. Furthermore, 4-5 years group values differed significantly from both 1 year and 20-35 years. In 5-6 weeks group, corneocytes were mostly arranged in thick packages, irregularly distributed over the surface. This changed already in 1 year-old children, where a homogenous distribution of superficial corneocytes was noted. In this age group, cells were most often encountered in clusters of 3 to 4 cells or dispersed individually. Such a pattern persisted in 4-5 years-old children and evolved slightly in adults. This morphological maturation pattern, consisting of an increase in corneocytes displaying central corneodesmosome labelling and an increase in the mean projected area of individual corneocytes, correlates with the increase in E.M.I. values previously observed by the present inventors.

TABLE 1

Demographics characteristics of the enrolled subjects
20 male or female volunteers
4 age groups - 5 subjects/group

| Age group | Mean Age (months) Mean ± SD |
|---|---|
| 5-6 weeks | 1.25 ± 0.14 |
| 1 year | 11.6 ± 1.52 |
| 4-5 years | 52.8 ± 6.57 |
| 20-35 years | 292.8 ± 16.1 |

TABLE 2

Quantitative assessment of most superficial corneocytes using immuno-SEM confirms age-related differences of the E.M.I. score.

| Age group | % corneocytes displaying "central" corneodesmosome labelling Mean ± SD | Mean projected area of individual corneocytes ($\mu m^2$) Mean ± SD |
|---|---|---|
| 5-6 weeks | 1.38 ± 0.08** | 646.3 ± 52.2a |
| 1 year | 8.90 ± 1.78* | 661.4 ± 33.6 |
| 4-5 years | 8.36 ± 0.74* | 723.2 ± 53.3b |
| 20-35 years | 7.34 ± 0.93* | 895.5 ± 67.8 |

Left column: Occurrence of corneocytes presenting "central" corneodesmosome labelling, in addition to the peripheral one, in four age groups.
**The 5-6 week-old value is significantly different from the others at $P < 0.01$;
*The groups 1 y.o., 4-5 y.o., and 20-35 y.o. differ from each other at $P < 0.05$.
Right column: Cell size of the most superficial corneocytes as measured in the four age groups: Mean projected area of individual corneocytes ($\mu m^2$) increases progressively with age.
avalues of 5-6 week-old and 20-35 y.o. are statistically different at $P < 0.01$;
b4-5 y.o. values differ significantly from both 1 y.o. and 20-35 y.o. at $P < 0.05$. (Mann-Whitney test).

The invention claimed is:

1. A method for determining whether the *stratum corneum* of a subject is mature or immature in its organization/function, said method comprising the steps of:
 a) taking a skin sample of said subject;
 b) determining the corneodesmosin distribution within the *stratum corneum* of the skin sample of step a) by an immunoelectron microscopy method, wherein said immunoelectron microscopy method comprises the steps of:
  i) contacting said skin sample with an antibody specific for corneodesmosin, wherein said antibody is labeled with a colloidal gold particle;
  ii) performing silver enhancement of the skin sample contacted with the antibody of step i); and
  iii) determining the fraction of corneocytes in the skin sample of step ii) displaying corneodesmosin localized centrally from the edge of said corneocytes;
 c) determining whether the *stratum corneum* of the subject is mature or immature in its organization/function based on the determination of step b), wherein
  a skin sample having 1.38%±0.08% corneocytes displaying central corneodesmosin of the total corneocytes indicates that said *stratum corneum* of the subject has maturity level of a subject aged 5-6 weeks in its organization/function.

2. The method of claim 1, wherein the skin sample is taken by stripping the skin surface.

3. The method of claim 1, wherein said colloidal gold particle is an ultrasmall gold particle.

4. The method of claim 1, wherein said immunoelectron microscopy method comprises a further step of detecting the labeled antibody bound to the sample by scanning electron microscopy.

* * * * *